United States Patent [19]
Sebti et al.

[11] Patent Number: 6,083,979
[45] Date of Patent: Jul. 4, 2000

[54] GERANYLGERANIOL/LOVASTATIN: A NOVEL APPROACH TO BLOCKING CANCER TRANSFORMATION WITHOUT CYTOTOXICITY

[75] Inventors: Said M. Sebti, Tampa, Fla.; Terence F. McGuire, Pittsburgh, Pa.

[73] Assignee: University of Pittsburgh, Pittsburgh, Pa.

[21] Appl. No.: 08/728,314

[22] Filed: Oct. 9, 1996

[51] Int. Cl.[7] .......................... A61K 31/35; A61K 31/045
[52] U.S. Cl. ............................................. 514/460; 514/739
[58] Field of Search ...................................... 514/460, 739

[56] References Cited

PUBLICATIONS

McGuire et al, J. Biol. Chem. (1996), 271(44), 27402–27407 Abstract Only.
Crick et al., SAAS Bull. Biochem. Biotechnol (1996), 9, 37–42 Abstract Only.

*Primary Examiner*—Jerome D. Goldberg
*Attorney, Agent, or Firm*—Cushman Darby & Cushman IP Group of Pillsbury Madison & Sutro

[57] ABSTRACT

Method of blocking aberrant Ras signaling in a mammal while avoiding excessive cell toxicity by administration of lovastatin and geranylgeraniol.

8 Claims, 7 Drawing Sheets

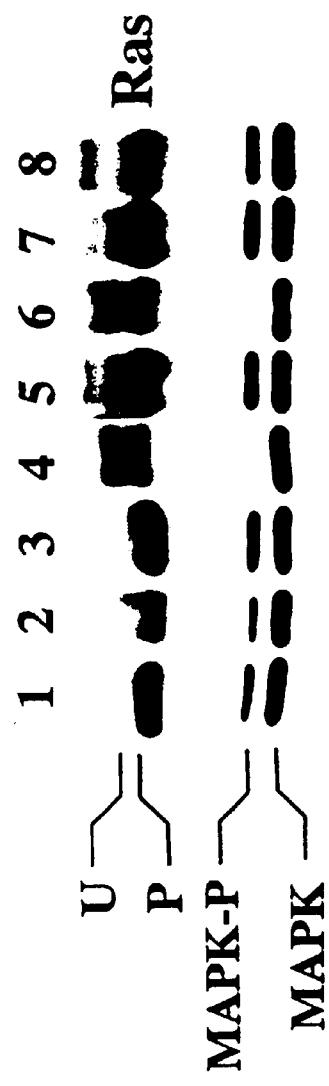
FIG. IA
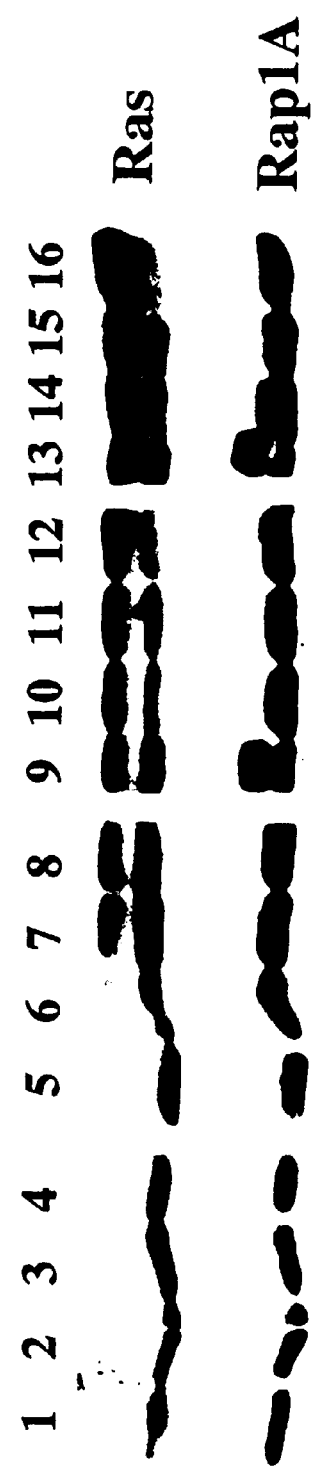
FIG. IB

FIG. 4A
FIG. 4B
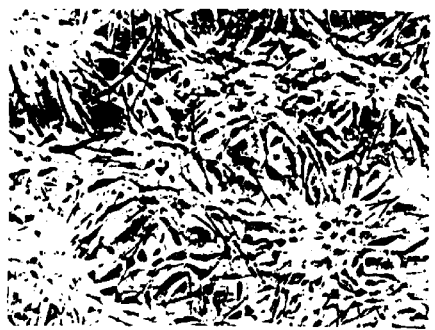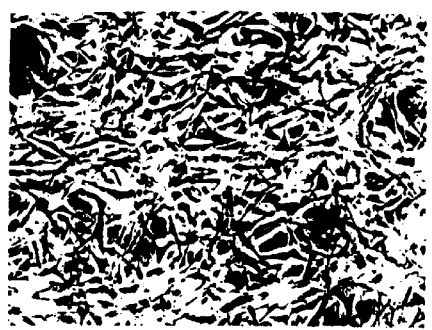
FIG. 4C
FIG. 4D
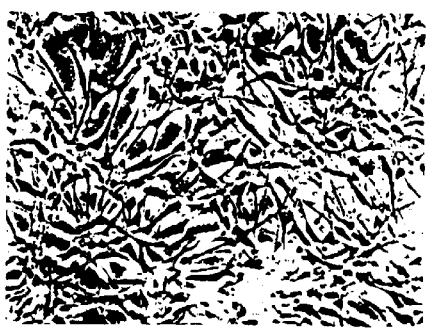
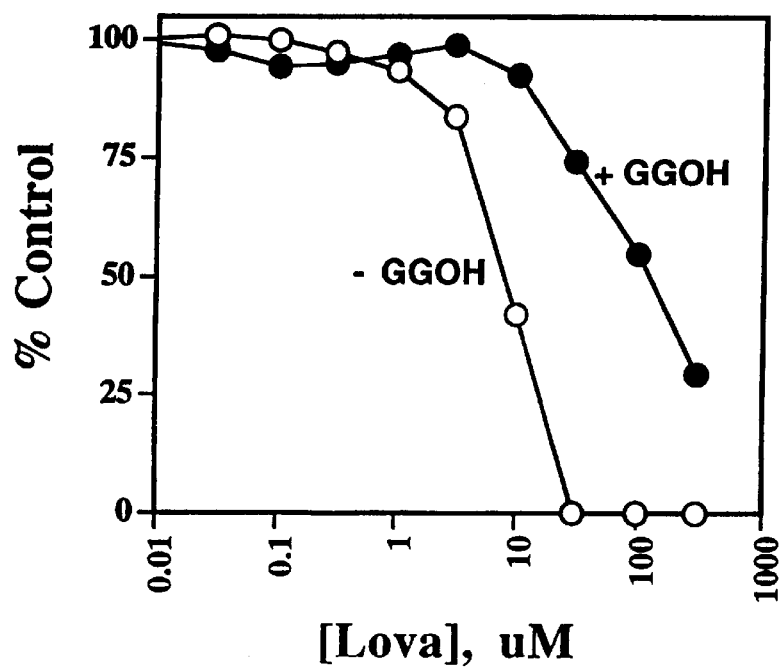
FIG. 4E 1  2    3  4

GERANYLGERANIOL/LOVASTATIN: A NOVEL APPROACH TO BLOCKING CANCER TRANSFORMATION WITHOUT CYTOTOXICITY

BACKGROUND OF THE INVENTION

1. Field of the Invention

The invention relates to a method of blocking aberrant Ras signaling in a mammal while avoiding excessive cell toxicity.

2. Background Information

The mevalonic acid (MVA) pathway is responsible for the biosynthesis of cholesterol and isoprenoid intermediates such as geranylgeranylpyrophosphate (GGPP) and farnesylpyrophosphate (FPP). Two sites in the MVA pathway have been cited to be of particular importance: the synthesis of MVA by 3-hydroxy-3-methylglutaryl-coenzyme A reductase (HMG-CoA reductase), an early step thought to be the major point of regulation, and the so-called "branch-point" of FPP metabolism (Brown and Goldstein 1980; Sabine, 1983; reviewed in Grunler et al., 1994). FPP is the last common intermediate in the pathway and is the substrate for a number of different enzymes that catalyze committed steps in branching pathways leading to the biosynthesis of cholesterol, ubiquinone, dolichol, as well as isoprenylated proteins and hemes. GGPP synthase, one of the branch-point enzymes, catalyzes the condensation of FPP and isopentenyl pyrophosphate to form GGPP. GGPP and FPP are utilized by geranylgeranyl-transferases (GGTases) I and II, and farnesyltransferase (FTase), respectively, for posttranslational isoprenylation of proteins on carboxyl terminal cysteine residues (reviewed in Maltese, 1990; Casey, 1992; Grunler et al., 1994). FTase and GGTase I prenylate proteins with carboxyl termini that end with a CAAX box where C=cysteine, A=aliphatic, and X=any amino acid. FTase prefers X as a serine or methionine whereas GGTase I prefers X as a leucine or isoleucine. GGTase II prenylates proteins that end in XXCC and XCX where X is any amino acid. For several proteins, isoprenylation is essential for proper intracellular localization and biological function (Holtz et al., 1989; Fukada et al. 1990; Der and Cox 1991; Hori et al. 1991; Inglese et al. 1992). In contrast to FPP, GGPP is currently known to be utilized only for protein prenylation.

Geranylgeranylated proteins and farnesylated proteins appear to comprise distinct but overlapping, sets of proteins, with the former being greater in number than the latter (Farnsworth et al., 1990; Epstein et al., 1990). Many of these proteins have been shown to play essential roles in signal transduction pathways and some have been implicated in malignant transformation. For example, the geranylgeranylated low molecular weight (20–28 KDa) guanine nucleotide-binding proteins Rho and Rac have recently been shown to be critical players in regulating not only the organization of the actin cytoskeleton (Nobes and Hall 1995) but also the progression of the cell cycle through Gl (Olson et al. 1995). In addition Ras, another family of guanine nucleotide-binding proteins, control normal cell growth (Mulcahy et al., 1985) and differentiation (Bar-Sagi and Feramisco, 1985) and, when mutated, can produce malignant transformation (Reddy et al., 1982). The Ras family of proteins serve as transducers of extracellular signals from receptor tysosine kinases to the nucleus (McCormick 1993). Their stimulation by these receptors results in the activation of several growth-related pathways including a cascade of mitogen-activated protein (MAP) kinases such as Raf, MEK and ERK (McCormick 1993), the latter of which can translocate to the nucleus and regulate the activity of some transcription factors. In some human cancers, Ras is GTP-locked and constitutively activates the MAPK cascade. Such cancers include, but are not limited to, colorectal, pancreatic and lung carcinomas, and melanoma.

The ability of Ras to cause cancer requires its attachment to the plasma membrane which is mediated by prenylation (Der and Cox 1991; Kato et al., 1992). The prenylation of Ras in vitro exhibits a preference for farnesylation (James et al, 1995). Furthermore although the prenylation of $K_B$-Ras in vivo is, at present, uncertain (Casey et al., 1989; Lerner et al., 1995b), H-Ras has been shown to require farnesylation for its cancer-causing activity (Hancock et al. 1989; Seabra et al., 1991; Lerner et al. 1995a). Moreover, in nude mice, inhibitors of FTase are effective at suppressing the growth of tumor cells possessing oncogenic H- or K-Ras (Sun et al., 1995).

Lovastatin is a potent competitive inhibitor of HMG-CoA reductase (Alberts 1988) and is used clinically as a cholesterol lowering agent. Following oral administration, the inactive lactone form is hydrolyzed to the β hydroxy acid form, which inhibits HMG-CoA reductase. HMG-CoA reductase catalyzes the reduction of HMG-CoA to mevalonate, an early rate-limiting step in the biosynthesis of cholesterol.

Lovastatin significantly reduces not only the biosynthesis of the end-product cholesterol for which it is used clinically (Illingworth and Bacon 1989), but also depletes the intracellular pools of GGPP and FPP, resulting in the inhibition of protein geranylgeranylation and protein farnesylation (Leonard et al., 1990). It has been recently discovered that lovastatin disrupts early signaling events such as tyrosine phosphorylation levels of the PDGF receptor and its association with PI-3-kinase (McGuire et al., 1993). Moreover, lovastatin arrests cultured cells predominantly in the $G_1$ phase of the cell cycle and produces a characteristic rounded morphology (Quesney-Hunecus et al., 1979; Sinensky and Logel, 1985; Fenton et al., 1992). Lovastatin has also been found to inhibit tumor growth of cells expressing oncogenic H-Ras in nude mice, but at doses that blocked tumor growth, the animals died (Sebti et al., 1991). It is not known whether inhibition of protein farnesylation and/or protein geranylgeranylation, or the reduction in levels of some other end-product of the MVA pathway, are responsible for lovastatin's toxicity.

SUMMARY OF THE INVENTION

The present invention uses lovastatin treatment of cells in conjunction with geranylgeraniol (GGOH) as a novel approach for selectively inhibiting aberrant Ras processing and signaling while rescuing cells from lovastatin toxicity. Accordingly, it is an object of the invention to provide a composition for blocking aberrant Ras signaling in a mammal while avoiding excessive cell toxicity.

The term mammal, as used herein, is intended to include all mammalian species. Most preferably, the methods and compositions of the invention are intended to be used for the treatment of humans.

As used herein, aberrant (or oncogenic) Ras signaling means the process by which farnesylated Ras sends a signal to the cell to divide uncontrollably.

Ras signaling is considered to be inhibited (blocked) when H-Ras farnesylation is blocked by at least about 10%, preferably by at least about 25%, more preferably by at least about 50%, and most preferably by at least about 90%.

By cell toxicity is meant adverse chemical effects on normal (noncancerous) cells which are sufficient to cause death of normal cells. By excessive toxicity is meant adverse effects on normal (noncancerous) cells which are sufficient to cause the death of the animal.

The composition of the invention comprises lovastatin in combination with geranylgeraniol, which when administered together to a mammalian cell have been unexpectedly found to enhance lovastatin's ability to block aberrant Ras farnesylation and signaling without the toxicity associated with the administration of lovastatin alone in amounts sufficient to inhibit Ras signaling.

In addition to the use of the invention to treat cancer with aberrant Ras function, other pathological conditions where Ras is involved could benefit from the invention. For example, Ras activation regulates smooth muscle cell proliferation and, therefore, the methods of the invention can be used for treating restenosis. Thus, another object of the present invention is to provide a method for treating or preventing restenosis in a human or lower mammal, comprising administering to the patient, in combination, therapeutically effective amounts of lovastatin and geranylgeraniol. The method can be used in any disease where a farnesylated protein is required since this method is effective at blocking protein farnesylation without affecting protein geranylgeranylation. For example, Hepatitis Delta Virus (HDV) large antigen must be farnesylated for the assembly of this virus. Thus, the method can be used to treat hepatitis delta virus infection.

Effective dosages for inhibition of Ras processing in accordance with the invention will be in the range of about 1 to 20 mg/kg daily for lovastatin, preferably about 1 to 10 mg/kg daily, and most preferably about 1 to 5 mg/kg daily; accompanied by dosages of about 1 to 20 mg/kg of geranylgeraniol, preferably about 1 to 10 mg/kg and most preferably about 1 to 5 mg/kg. The ratio of lovastatin to geranylgeraniol will vary, most preferably being between about 1:1 (equimolar) to 1:2. Exact dosages will depend on the extent to which the compounds are metabolized as well as their bioavailability to the target tissue. Appropriate doses in individual cases can be determined by persons of ordinary skill in the art. Lovastatin and geranylgeraniol can be administered according to the present invention in formulations with suitable diluents, carriers, preservatives, colorants and the like, which are known to those of skill in the pharmaceutical arts. Such formulations are currently available for lovastatin (Physician's Desk Reference, 50th Ed., 1996, Medical Economics, Montvale, N.J., p. 1699).

The invention includes compositions in which lovastatin and geranylgeraniol are combined into one pharmaceutical, using binders, carriers and other additional agents which are known to those of skill in the pharmaceutical arts.

BRIEF DESCRIPTION OF THE DRAWINGS

FIGS. 1 (A and B). GGOH potentiates lovastatin-induced inhibition of H-Ras-CVLS processing and signaling while rescuing that of H-Ras-CVLL.

FIG. 1A: NIH-3T3 cells transformed with either H-Ras-CVLS(61L) (lanes 1–4) or H-Ras-CVLL(61L) (lanes 5–8) were treated 2 consecutive days with vehicle (lanes 1 and 5), lovastatin (20 μM on day 1 and 10 μM on day 2) (lanes 2, 4, 6, and 8), and 20 μM GGOH (lanes 3, 4, 7, and 8). Cells were lysed and equivalent amounts of protein electrophoresed and immunoblotted with either anti-Ras antibody (Y13-238) or anti-MAPK as described in Example 3. The slower-migrating, unprocessed form (U) and the processed form (P) of Ras as well as the inactive and activated forms of MAPK (MAPK and MAPK-P, respectively) are indicated. Data are representative of 3 independent experiments.

FIG. 1B: NIH-3T3 cells transformed with H-Ras-CVLS (61L) were treated 2 consecutive days with vehicle (lanes 1–4) or with lovastatin at 1 μM (lanes 5–8), 5 μM (lanes 9–12), or 15 μM (lanes 13–16) in conjunction with GGOH at either 0 μM (lanes 1, 5, 9, and 13), 7.5 μM (lanes 2, 6, 10, and 14), 15 μM (lanes 3, 7, 11, and 15), or 30 μM (lanes 4, 8, 12, and 16). Cells were lysed and equivalent amounts of protein electrophoresed and immunoblotted with anti-Ras antibody (Y13-238). The identical membrane was then reprobed with anti-RaplA antibody. Data are representative of 2 independent experiments.

FIGS. 4 (A–D). GGOH prevents lovastatin-induced cell rounding and cytotoxicity in NIH-3T3 cells transfected with oncogenic H-Ras-CVLS. NIH-3T3 cells transformed with Ras were plated and then were treated 2 consecutive days with either vehicle (4A), 40 μM GGOH (4B), 20 μM lovastatin (4C), or both 40 μM GGOH and 20 μM lovastatin (4D).

FIG. 4E: Cells were plated into 96-well plates (10,000 cells/well) and the following day were treated with various concentrations of lovastatin (0–300 μM) in the presence and absence of 15 μM GGOH. After 4 days, medium was removed from cells and replaced with fresh medium containing 1 mg/ml 3-[4,5-dimethylthiazol-2-yl]-2,5-diphenyltetrazolium bromide (MTT) for 3 h. The number of viable cells was determined by the MTT assay described in Example 2. Data are representative of 3 independent experiments.

FIG. 6. $^3$H-GGOH metabolic labeling of proteins. NIH-3T3 cells transformed with Ras were metabolically labeled for 21–22 h with 0.6 μM $^3$H-GGOH (30 μCi/ml) in the presence of 20 μM lovastatin and in the absence (lane 1) or the presence (lanes 2–4) of 4.4 μM unlabeled GGOH. In addition, some cells were pre-treated (overnight) with 20 μM lovastatin prior to metabolic labeling (lane 4). Data shown in lanes 1 and 2 was obtained from one experiment in which the samples contained 25,600 cpm and 40,300 cpm, respectively: data shown in lanes 3 and 4 was from a separate experiment in which the samples contained 64,300 cpm and 98,400 cpm, respectively. Fluorography was performed on the dried gels (described in Example 4) using 16-day (lanes 1 and 2) and 2.5-day (lanes 3 and 4) exposures at −80° C. Data are representative of 2 independent experiments.

FIG. 7. Effect of GGOH on lovastatin-induced accumulation of GGTase I protein substrates in the cytosol. The cytosolic (60S) fraction was obtained from NIH-3T3 cells treated with vehicle (lane 1), 25 μM GGOH (lanes 2 and 4) and 50 μM lovastatin (lanes 3 and 4) and used as the source of protein substrates for an in vitro geranylgeranylation assay as described in Example 5. Equivalent amounts of protein (160 μg) were used for each sample. Recombinant, non-prenylated H-Ras-CVLL (2.5 μg; lane 5) was used as a positive control.

DETAILED DESCRIPTION OF THE INVENTION

Figure 2:
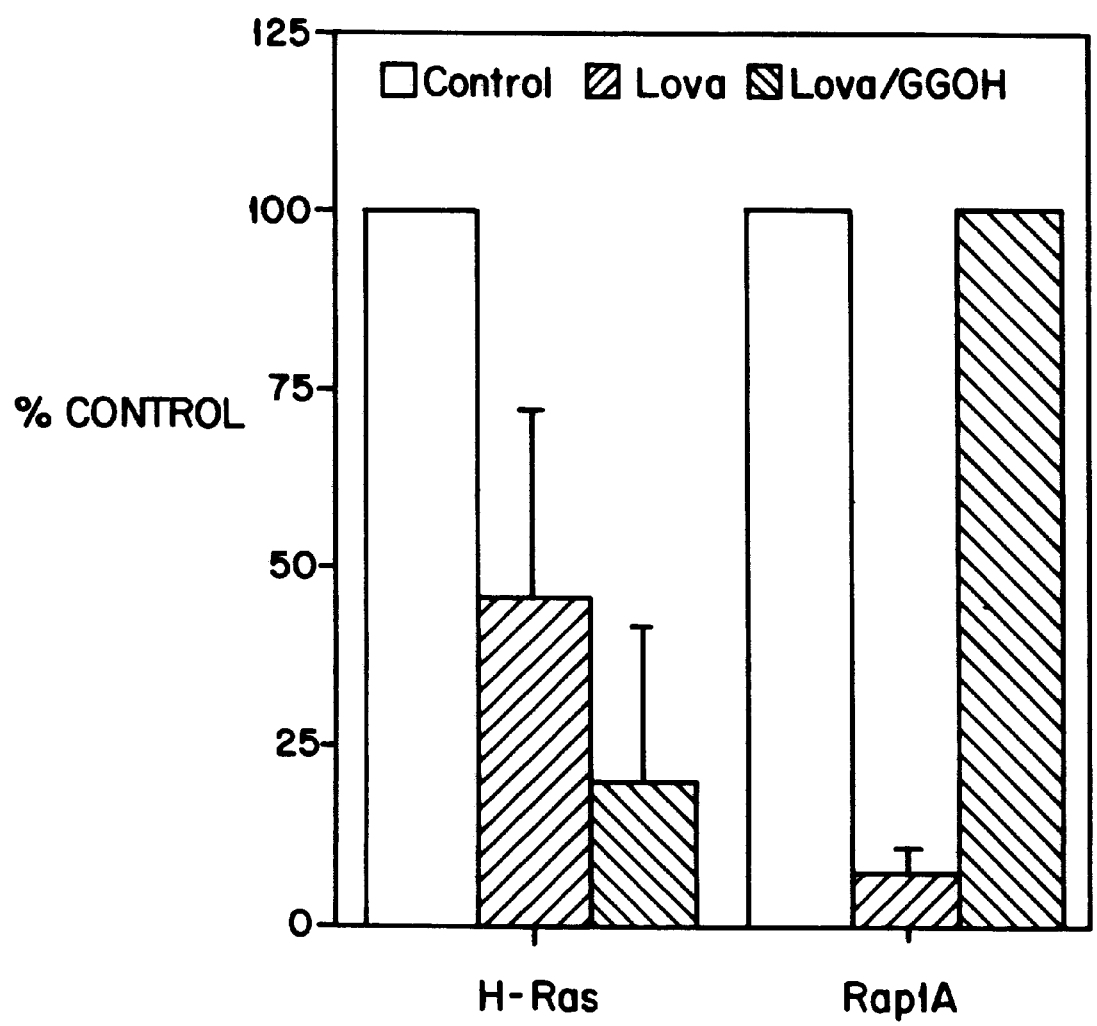
FIG. 2. Opposing effects of lovastatin/GGOH co-treatment on Ras and RaplA processing. Graphical representation of results from 3 independent experiments (data shown in Table I) illustrating the divergent effects of GGOH on H-Ras and RaplA processing in lovastatin-treated cells.

Lovastatin was obtained from Merck. Geranylgeraniol was obtained as mixed isomers from Sigma Chemical Co. or the all-trans isomer from American Radiolabelled Chemicals, Inc. Both agents were prepared as stock solutions in dimethylsulfoxide (DMSO) with 10 mM dithiothreitol (DTT). DTT is not expected to be necessary in the formulation, since neither lovastatin nor GGOH possesses a thiol functional group.

For convenience, the following abbreviations are used in the specification: FTase, farnesyltransferase; GGTase, geranylgeranyltransferase; FPP, farnesylpyrophosphate; GGPP, geranylgeranylpyrophosphate; GGOH, geranylgeraniol; HMG-CoA, hydroxymethylglutaryl-coenzyme A; SDS-PAGE, sodium dodecyl sulfate polyacrylamide gel electrophoresis; MAPK, mitogen-activated protein kinase; DTT, dithiothreitol; DMSO, dimethylsulfoxide; PMSF, phenylmethylsulfonyl fluoride; MVA, mevalonic acid; PBS, phosphate-buffered saline; CAAX, C=cysteine, A=aliphatic, X=any amino acid; MTT, 3-[4,5-dimethylthiazol-2-yl]-2,5-diphenyltetrazolium bromide.

EXAMPLE 1
Cell Culture

NIH-3T3 mouse fibroblasts (ATCC) were maintained in Dulbecco's modified Eagles medium (DMEM) supplemented with 10% fetal bovine serum and 1% Pen-Strep (Life Technologies Inc.). NIH-3T3 cells transfected with the oncogene encoding H-Ras-CVLS(12R) or H-Ras-CVLS (61L) or with the empty vector (pZIPneo) were kind gifts from Dr. Channing Der and Dr. Adrienne Cox (University of North Carolina, Chapel Hill) and were maintained in DMEM supplemented with 10% calf serum, 1% Pen-Strep, and 400 μg/ml G418.

EXAMPLE 2
MTT Cytotoxicity Assay

NIH-3T3 cells transfected with either the H-Ras-CVLS (61L) oncogene or the empty vector were seeded into 96-well plates (10,000/well) and the following day treated (at 50–70% confluency) with increasing concentrations of lovastatin (0–300 μM) in the presence or the absence of 15 μM GGOH. After 4 days, the medium was replaced with 100 μl of MTT (1 mg/ml) in DMEM. After 3 h incubation at 37° C. the tetrazolium/formazan reaction was stopped and the uptake of MTT assessed by replacing the medium with 100 μl DMSO, shaking the plate for 5 min to solubilize all the dye, and measuring the absorbance at 492 nm with a Titertek Multiskan spectrophotometer (Flow Laboratories, McClean Va.).

EXAMPLE 3
Immunoblotting to Assess Protein Processing and MAP Kinase Activation Cells were seeded into 100 mm plates ($8.0 \times 10^5$–$1.0 \times 10^6$/plate) on day 0 such that the following day they were 50–70% confluent. Cells were treated twice (days 1 and 2) with vehicle (10 mM DTT in DMSO) or concentrations of lovastatin and/or GGOH as indicated in the figure legends. On day 3, cells were harvested in ice cold PBS, pH 7.5, pelleted, and then lysed in 50 mM HEPES, pH 7.5, 10 mM NaCl, 1% Triton X-100, 10% glycerol, 5 mM $MgCl_2$, 1 mM EGTA, 25 μg/ml leupeptin, 2 mM $Na_3VO_4$, 1 mg/ml soybean trypsin inhibitor, 10 μg/ml aprotinin and 6.4 mg/ml phosphatase substrate. After clearing the lysates (14,000 rpm, 4° C., 10 min), equivalent amounts of protein were applied to SDS-polyacrylamide gels (12.5% for protein processing; 15% for MAP kinase), separated by electrophoresis, and subsequently transferred to nitrocellulose filters. Filters were blocked with 5% non-fat dry milk in PBS, 0.1% Tween-20 (PBS-T) and then probed with either anti-Ras (Y13-238 or Y13-259, ATCC), anti-RaplA (Santa Cruz Biotechnology, Santa Cruz, Calif.) anti-RhoB (Santa Cruz Biotechnology, Santa Cruz, Calif.), anti-Rab5 (Transduction Laboratories, Lexington, Ky.) or anti-MAP kinase (erk2, UBI, Lake Placid, N.Y.) antibodies in 3% non-fat dry milk in PBS-T. Positive antibody reactions were detected using appropriate horseradish peroxidase-conjugated antibodies (Oncogene Science and Jackson ImmunoResearch Laboratories Inc., West Grove, Pa.) and an enhanced chemiluminescence detection system (ECL, Amersham Corp.).

EXAMPLE 4
$^3$-H-GGOH Metabolic Labeling of Cellular Proteins

NIH-3T3 cells transfected with H-Ras-CVLS(61L) were seeded into 12-well plates (200,000 cells/well) and incubated the following day (at 90–100% confluency) with tritiated GGOH in a manner similar to that described by Crick et al. (1994). Cells were incubated with 500 μl DMEM medium containing 30 μCi/ml $^3$H-GGOH (50–60 Ci/mmole; 0.6 μM GGOH, final), 3–5% calf serum and 20 μM lovastatin. As noted in the legend to FIG. 6, some cells were treated with additional unlabeled GGOH which increased the final GGOH concentration to 5 μM but decreased the specific activity by 8.7-fold. In addition, some cells were treated overnight with 20 μM lovastatin prior to incubation with the labeled GGOH. After 21–22 h at 37° C., the labeling medium was removed and the cells were washed once with 1.5 ml ice-cold PBS, pH 7.5 and harvested using two 1.0-ml aliquots of ice-cold PBS, pH 7.5. The cells were spun down and the pellets were disrupted in ice-cold $CH_3OH$. The delipidated protein pellets were extracted twice with $CHCl_3/CH_3OH$ (2:1), air dried and subsequently dissolved in 95 μl SDS-PAGE sample buffer. An aliquot (5 μl) was used to determine the amount of tritium incorporated into protein and the remainder loaded onto a 12.5% SDS-polyacrylamide gel. After electrophoretically separating the labeled proteins, the gels were fixed with $CH_3OH$/$CH_3CO_2H/H_2O$ (9:2:9), treated with ENTENSIFY (DuPont NEN, Boston, Mass.), dried down on Whatman paper, and exposed to X-ray film for 2–16 days at −80° C.

EXAMPLE 5
In Vitro GGTase I Assay of 60S Proteins

NIH-3T3 cells were seeded into 100 mm plates (3.8×10$^6$ cells/plate) and were treated the following day (about 70% confluency) with either vehicle, 25 µM GGOH, 50 µM lovastatin, or 50 µM lovastatin and 25 µM GGOH. After 40 h, the cells were washed, harvested in ice-cold PBS, pH 7.5, and the cell pellet volume (PV) estimated. Cells were disrupted by sonication in 1.4×PV of 50 mM TRIS, pH 7.5, 1 mM EGTA, 1 mM DTT, 1 mM PMSF, 25 µg/ml leupeptin, and 10 µg/ml aprotinin and the cytosolic (60S) fraction prepared by centrifugation at 25,000 rpm for 1 h at 4° C. using a Beckman SWT155 swinging bucket rotor. Equivalent amounts of cytosolic protein (160 µg) were incubated in 50 mM TRIS, pH7.5, 50 µM ZnCl$_2$, 20 mM KCl, 3 mM MgCl$_2$, 1 mM DTT with exogenously added human GGTase I (Mono Q-purified from human Burkitt Lymphoma (Daudi) cells). Prenylation of 60S proteins was started by addition of 4.8 µCi $^3$H-GGPP and the reaction allowed to proceed for 45–60 min at 37° C. Total reaction volume was 55.4 µl. The reaction was stopped by briefly placing tubes on ice and then adding 25 µl SDS-PAGE sample buffer (2×). Samples were electrophoresed on 12.5% SDS-polyacrylamide gels and the gels processed for fluorography as described above for $^3$H-GGOH metabolic labeling.

EXAMPLE 6
Lovastatin/GGOH Co-treatment Selectively Inhibits Oncogenic H-Ras Processing and Signaling The effects of GGOH on lovastatin inhibition of protein farnesylation were investigated in NIH-3T3 cells transformed with an oncogenic, GTP-locked mutant of H-Ras-CVLS (an FTase substrate). Cells were treated with lovastatin and GGOH alone or in combination, and the extent of oncogenic Ras processing, as well as its ability to stimulate MAPK, were assessed. NIH-3T3 cells transformed with oncogenic H-Ras-CVLL (mutated at its CAAX box to become a GGTase I substrate) were treated in parallel with those transformed by oncogenic H-Ras-CVLS and served as a control exhibiting processing and signaling that is geranylgeranylation-dependent. After 2 days of treatment, the cells were harvested and lysed and the lysate proteins subsequently separated by SDS-PAGE and immunoblotted with anti-Ras or anti-MAPK antibodies as described in Example 3. Cells treated with vehicle or GGOH alone exhibited only the processed form of Ras and both the active (hyperphosphorylated) and inactive (hypophosphorylated) forms of MAPK (FIG. 1A, lanes 1 and 5). Lovastatin partially inhibited the processing of both H-Ras-CVLS and H-Ras-CVLL and inhibited the activation of MAPK slightly in H-Ras-CVLS-transformed cells and completely in H-Ras-CVLL-transformed cells (FIG. 1A, lanes 2 and 6). While co-treatment with GGOH completely prevented the inhibitory effect of lovastatin in H-Ras-CVLL-transformed cells, H-Ras-CVLS processing and MAPK activation were inhibited to an extent that was greater than that observed for lovastatin treatment alone (FIG. 1A, lanes 4 and 8). To assess the sensitivity of protein farnesylation to inhibition by lovastatin/GGOH co-treatment, cells were treated with various concentrations of both compounds, and the extent of H-Ras processing assessed. As shown in FIG. 1B, GGOH treatment alone (0–30 µM; lanes 1–4) as well as 1 µM lovastatin alone (lane 5) did not inhibit H-Ras processing. However, co-treatment of cells with 1 µM lovastatin and 7.5 µM GGOH (FIG. 1B, lane 6) achieved detectable inhibition of Ras processing; significant inhibition was observed with the same concentration of lovastatin and 30 µM GGOH (lane 8). While treatment of cells with 5 µM and 15 µM lovastatin produced a partial inhibition of Ras processing, co-treatment with 7.5 µM GGOH resulted in a much greater inhibition (FIG. 1B, lanes 9–16). Co-treatment of cells with lovastatin/GGOH (15 µM/30 µM) was observed to completely inhibit Ras processing (FIG. 1B, lane 16). When the same nitrocellulose membrane was reprobed with an antibody against Rap1A, the processing of this endogenous geranylgeranylated protein was observed to be significantly inhibited at 5 µM and 15 µM lovastatin (FIG. 1B, lanes 9 and 13), but was restored upon co-treatment with GGOH at even 7.5 µM (lanes 10 and 14).

These dramatic and divergent effects of GGOH on lovastatin inhibition of oncogenic Ras and Rap1A processing are depicted graphically in FIG. 2. Based on three independent experiments (Table I), cells treated with 15 µM lovastatin demonstrated an inhibition of H-Ras processing of 54%, and of Rap1A processing of 93%. Co-treatment with 15 µM lovastatin and 15 µM GGOH further reduced levels of processed oncogenic Ras to 20% while those of Rap1A were completely restored. Analysis of the data in Table I using a Student's two-tailed paired t-test demonstrates that the inhibition of oncogenic Ras processing achieved by lovastatin/GGOH co-treatment is statistically different (p<0.01) from that achieved by lovastatin treatment alone. Hence, by employing this treatment with cells that express constitutively activated Ras, the processing and signaling of this oncoprotein can be potently inhibited without affecting the processing/function of geranylgeranylated proteins.

Table I. Data from Three Independent Experiments Illustrating the Divergent Effects of GGOH on Ras and Rap1A Processing in Lovastatin-treated Cells.

| | % of processed Ras | | | % of processed Rap1A | | |
|---|---|---|---|---|---|---|
| Expt. | control | lova | lova + GGOH | control | lova | lova + GGOH |
| 1 | 100 | 27 | 5 | 100 | 9 | 100 |
| 2 | 100 | 36 | 9 | 100 | 9 | 100 |
| 3 | 100 | 75 | 45 | 100 | 4 | 100 |

The processing of Ras and Rap1A was assessed after treating cells 2 days with either vehicle (control), 15 µM lovastatin, or both 15 µM GGOH and 15 µM lovastatin. Statistical analysis of the data obtained from these experiments demonstrated that the inhibition of Ras processing effected by lovastatin/GGOH cotreatment is statistically different from that achieved by using lovastatin alone (p<0.01 using a Student's two-tailed paired t-test).

Figure 3:
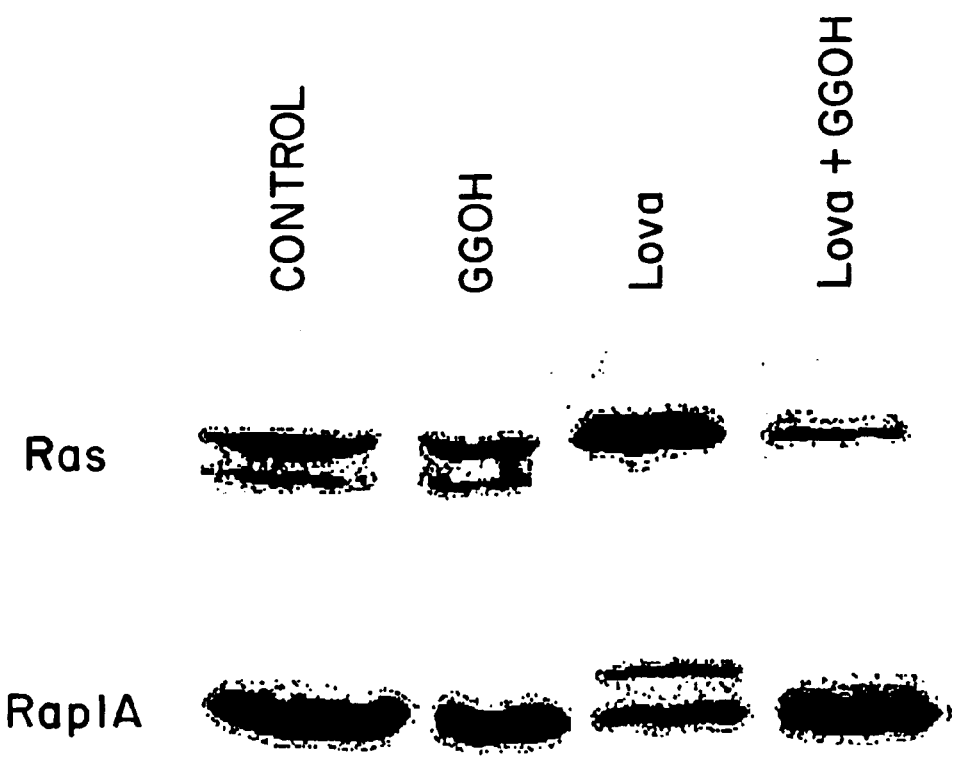
FIG. 3. Lovastatin/GGOH co-treatment achieves complete inhibition of one form of Ras expressed in human lung carcinoma cells (A549 cells). The processing of Ras and RaplA was assessed in A549 cells after 2 days of treatment with either vehicle (control, lane 1), 30 μM GGOH (lane 2), 30 μM lovastatin (lane 3), or both 30 μM GGOH and 30 μM lovastatin (lane 4).

EXAMPLE 7
Lovastatin/GGOH Co-treatment Inhibits the Processing of Ras but not that of Rap1A in Human Lung Carcinoma Cells In an effort to demonstrate that lovastatin/GGOH co-treatment is an effective means of inhibiting the processing of Ras in human cancer cells, human lung carcinoma (A549) cells were treated 2 days with lovastatin and GGOH alone and in combination and the extent of processing for Ras and Rap1A assessed. When cell lysates were electrophoresed and immunoblotted with anti-Ras antibodies, two distinct bands of Ras were detected in control cells (FIG. 3, lane 1). As shown in FIG. 3, the processing of the Ras protein corresponding to the faster-migrating (lower) band, as well as that of the endogenous Rap1A in the same cells, was observed to be sensitive to treatment with lovastatin alone (lane 3). However, in cells co-treated with lovastatin and GGOH, inhibition of processing of the lower Ras band was still observed but that of RaplA was restored (lane 4). These results, therefore, show the efficacy of the lovastatin/ GGOH co-treatment toward inhibition of processing of Ras, but not RaplA, in a human cancer line.

EXAMPLE 8

Figure 5:
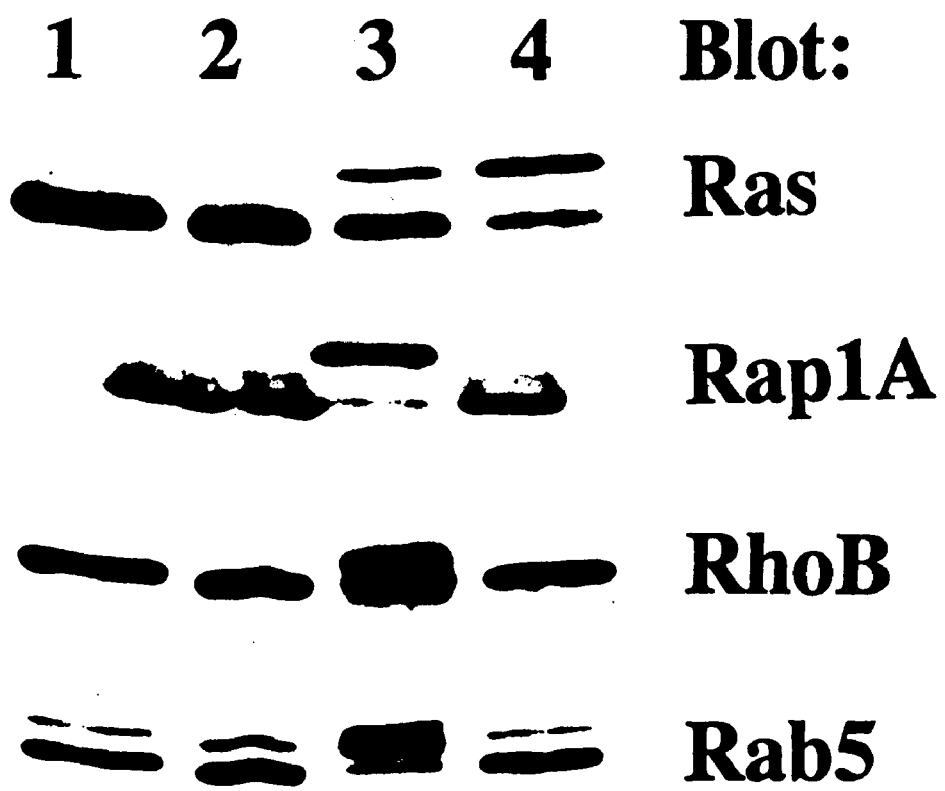
FIG. 5. GGOH rescues lovastatin-induced inhibition of geranylgeranylated protein processing. The identical cells shown in FIG. 4A were harvested, lysed, and whole cell lysate protein (50 μg) was electrophoresed and immunoblotted for Ras, RaplA, RhoB, and Rab5 using appropriate antibodies as described in Example 3. Lanes 1–4 represent cells treated with vehicle, 40 μM GGOH, 20 μM lovastatin, or both 40 μM GGOH and 20 μM lovastatin, respectively.

Geranylgeraniol (GGOH) Rescues Lovastatin-induced Cell Rounding, Cytoxicity, and Inhibition of Processing of Geranylgeranylated Proteins Ras-transformed NIH-3T3 cells were treated with lovastatin, GGOH, or a combination of both. FIG. 4A–4D illustrate the characteristic rounded cell morphology produced by treatment of cells with lovastatin alone, as well as the complete prevention of this change by co-treatment with GGOH. Since lovastatin is known to be cytotoxic at concentrations that cause cell rounding, we investigated whether GGOH could attenuate lovastatin cytotoxicity. Cells were plated at high density in 96-well plates and treated with various concentrations of lovastatin alone or in combination with GGOH. FIG. 4E shows that while lovastatin inhibited Ras-transformed 3T3 cell growth with an $IC_{50}$ of 8 $\mu$M, co-treatment with GGOH (15 $\mu$M) significantly attenuated lovastatin cytotoxicity, increasing the $IC_{50}$ by 15-fold. These findings were similar for all cell lines tested, both non-transformed and transformed. The rounding of cells induced by lovastatin has been suggested to be due to its inhibitory effects on protein geranylgeranylation (Fenton et al., 1992). Rho and Rac proteins, both of which are geranylgeranylated, have been demonstrated to regulate polymerization of actin and to play a pivotal role in maintaining cellular shape (Nobes and Hall 1995). Thus the ability of GGOH to prevent lovastatin-induced rounding suggested that it might be serving to preserve protein geranylgeranylation by replenishing the depleted pool of geranylgeranyl in lovastatin-treated cells. In order to address whether the processing of geranylgeranylated proteins is indeed rescued by co-treatment with GGOH, cells were treated with either lovastatin alone, GGOH alone, or a combination of both, and the processing of RaplA and RhoB (substrates for GGTase I) and Rab5 (a GGTase II substrate) was assessed. FIG. 5 shows that while the processing of all of these proteins was inhibited by lovastatin, no detectable inhibition of processing was observed when cells were co-treated with both lovastatin and GGOH. These findings strongly suggest that GGOH is converted to a metabolite that can be utilized by GGTases for protein geranylgeranylation.

EXAMPLE 9

Metabolic Labeling of Proteins Using $^3$H-GGOH

In order to establish that GGOH was being used as metabolic source for protein prenylation in mouse fibroblasts, Ras-transformed NIH-3T3 cells were treated with $^3$H-GGOH and 20 $\mu$M lovastatin for 20 h and the delipidated proteins were separated by SDS-PAGE and visualized by fluorography. As shown in FIG. 6 (lane 3) a pattern of labeled proteins (MW range of 21–29 kDa) resembling that obtained for small G proteins was observed. Although treatment of cells with lovastatin at the time of $^3$H-GGOH labeling did not significantly enhance tritium incorporation into protein (data not shown), pre-treatment of cells with 20 $\mu$M lovastatin for 24 h before co-treatment with lovastatin and $^3$H-GGOH did significantly increase protein labeling (FIG. 6, lane 4). In addition, optimal metabolic labeling of protein was found to occur when unlabeled GGOH was added such that the final concentration was increased from 0.6 $\mu$M ($^3$H-GGOH alone) to 5.0 $\mu$M (FIG. 6, lanes 1 and 2). Hence although the specific activity of $^3$H-GGOH was decreased approximately 8-fold by addition of unlabeled GGOH, increased tritium incorporation was observed. Presumably, this is due to kinetic factors involved in the conversion of GGOH to an activated form and/or the use of this activated form for protein prenylation. Further addition of unlabeled GGOH (10 $\mu$M, final) did not result in a further increase in protein labeling (data not shown). These results suggest that GGOH is being metabolically converted by mouse fibroblasts to an activated form (possibly GGPP) and used for protein geranylgeranylation. This form replenishes the GGPP pool that is depleted in lovastatin-treated cells.

EXAMPLE 10

GGOH Co-treatment Significantly Reduces the Levels of all Unprocessed GGTase I Protein Substrates in the Cytosolic Fraction of Lovastatin-treated NIH-3T3 cells The effect of GGOH co-treatment on the processing of all GGTase I protein substrates in NIH-3T3 cells was assessed using a novel approach. Cells were treated with lovastatin (50 $\mu$M) and GGOH (25 $\mu$M) alone or in combination, harvested, and cytosolic fractions prepared and used as a source of protein substrates in an in vitro geranylgeranylation assay. As shown in FIG. 7, the cytosolic fractions obtained from cells treated with vehicle or GGOH alone contained no unprocessed proteins capable of serving as substrates in the in vitro assay (lanes 1 and 2). However, the cytosolic fractions from lovastatin-treated NIH-3T3 cells contained several protein substrates for GGTase I, as demonstrated by the profile of tritium-labeled geranylgeranylated proteins ranging from 21–29 kDa that was detected using this assay (FIG. 7, lane 3). When the assay was performed on the cytosolic fractions from NIH-3T3 cells co-treated with lovastatin and GGOH, all of the protein substrates for GGTase I (detected in the cytosolic fractions from lovastatin-treated cells) were observed to be significantly reduced (FIG. 7, lane 4). In longer exposures, a few other bands of higher and lower molecular weight appeared in the lane containing cytosol from lovastatin-treated cells but these also were not detected in the cytosol from cells co-treated with lovastatin and geranylgeraniol. Thus, this novel approach demonstrates that GGOH is converted by the cells to a form capable of rescuing the processing of virtually all proteins that are geranylgeranylated by GGTase I in the cell.

Discussion

The examples presented herein clearly demonstrate that simultaneous lovastatin and GGOH treatment of cells preserves the processing of geranylgeranylated proteins while that of farnesylated Ras is further inhibited (FIGS. 1 and 5) above that which occurs after lovastatin treatment alone. The fact that GGOH has no apparent effect on protein prenylation in the absence of lovastatin (FIGS. 1, 5 and 7) indicates that it acts to replenish the pool of GGPP or to provide an acceptable substitute. This is consistent with data from Crick et al. (1994) who previously demonstrated that when $^3$H-GGOH metabolically-labeled proteins were subjected to Pronase E digestion, a labeled product that was chromatographically identical to geranylgeranylcysteine was released. By achieving the selective restoration of protein geranylgeranylation, not only can cell morphology be maintained at the same phenotype as control cells (FIGS. 4A–4D), but much of the cytotoxic effects of lovastatin can be alleviated (FIG. 4E). The maintenance of cell shape as well as cell cycle progression through $G_1$ might be expected since these cellular processes have recently been shown to be regulated by geranylgeranylated proteins (Rho and Rac; Nobes and Hall, 1995; Olson et al 1995). Thus, GGOH enhances the inhibitory effect of lovastatin on the uncontrolled signalling caused by farnesylated oncogenic Ras while preserving normal cellular functions that are dependent on geranylgeranylated proteins.

Figure 8:
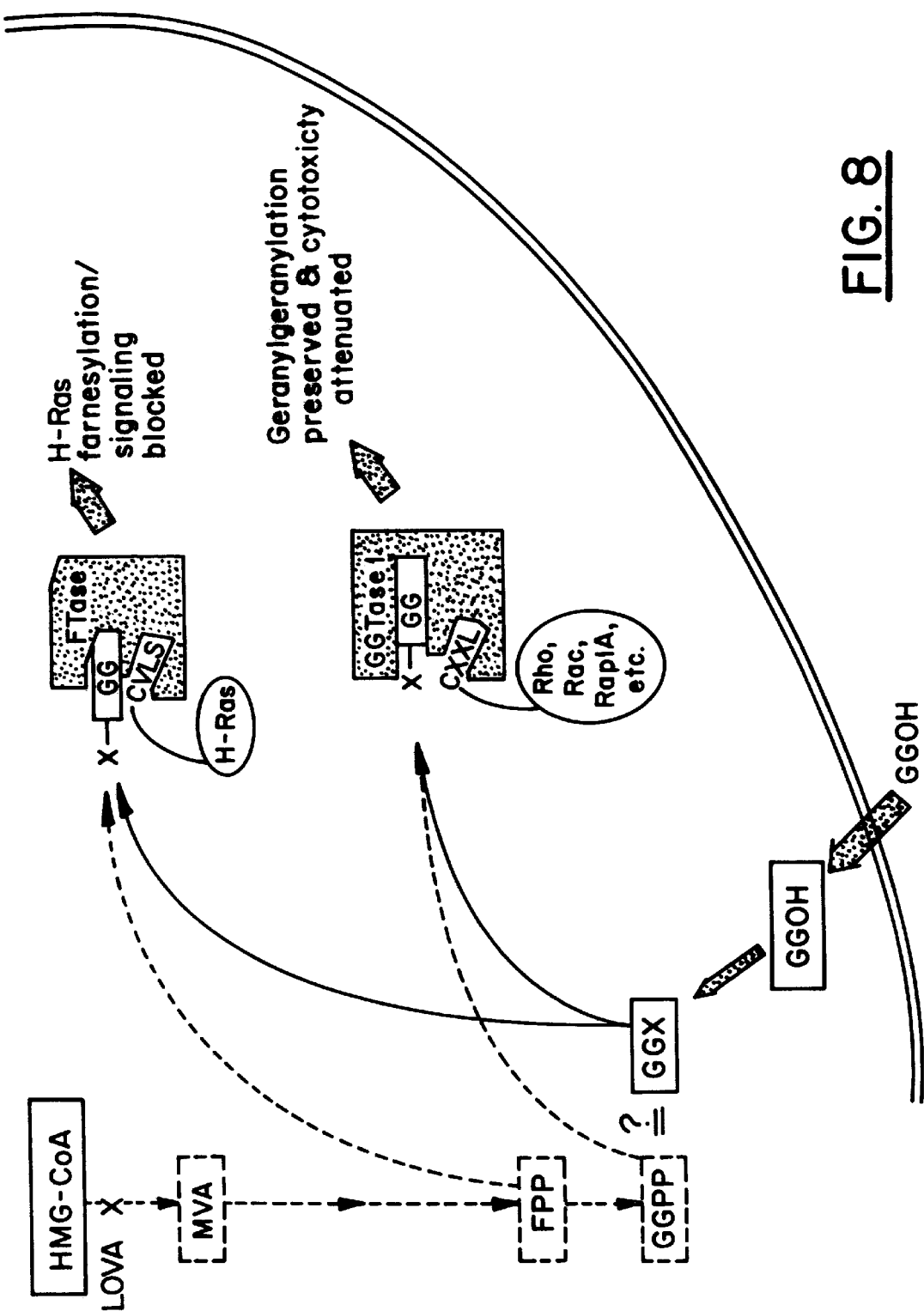
FIG. 8. A proposed model depicting the mechanism by which GGOH acts, in the presence of lovastatin, to preserve protein geranylgeranylation and concomitantly potentiate inhibition of protein farnesylation. Dashed lines indicate the inhibition of FPP and GGPP biosynthesis via the MVA pathway upon treatment with lovastatin. GGOH is taken up by cells and is converted to a metabolite GGX that serves as an inhibitor of FTase and as a substrate for GGTase I and GGTase II.

Based on the results presented here, we have proposed a model depicting the mechanism by which GGOH confers to lovastatin a selective and enhanced ability to inhibit protein farnesylation (FIG. 8). As discussed above, GGOH is suggested to be taken up and converted by cells to an activated form (designated GGX in FIG. 8) which serves as the geranylgeranyl donor for protein prenylation catalyzed by GGTases I and II (only GGTase I is depicted in FIG. 8). Moreover, GGX is proposed to competitively inhibit FPP from the active site of FTase. Previous work shows that GGPP can bind to the active site of FTase with a similar affinity to that of FPP but cannot be used as a substrate for protein prenylation (Reiss et al., 1992). Moreover, it has been demonstrated in vitro that GGPP inhibits FTase with an $IC_{50}$ of 5 $\mu M$ (unpublished data). Thus, in the presence of lovastatin endogenous pools of FPP are low and GGX can act to potently inhibit FTase (FIG. 8): in the absence of lovastatin, no inhibition of Ras processing is observed since the levels of GGX formed are not high enough to compete out endogenous FPP from the FTase active site (FIGS. 1 and 5).

The examples presented herein demonstrate that lovastatin-induced cell rounding and cytotoxicity are not due to inhibition of protein farnesylation. More importantly, the data indicate that inhibition of protein geranylgeranylation by lovastatin is solely responsible for these untoward effects. Therefore, the novel approach of the present invention is a powerful tool for selectively inhibiting oncogenic Ras signaling while sparing cells from lovastatin cytotoxicity. It should be a safe and effective treatment for cancers and other pathological conditions which are related to H-Ras signaling as well as any pathological condition which depends on a protein that requires farnesylation for its function/activity (e.g. HDV large antigen).

For convenience, references cited herein are set forth below in their entirety and are hereby incorporated by reference.

References

Adamson, P., Marshall, C. J. Hall, A., and Tilbrook, P. A. (1992). Post-translational modifications of p21$^{rho}$ proteins. J. Biol. Chem. 267, 20033–20038.

Alberts, A. W. (1988). Discovery, biochemistry and biology of lovastatin. Am. J. Cardiol. 62, 10J-lSJ.

Bar-Sagi, D., and Feramisco, J. R. (1985). Microinjection of the ras oncogene protein into PC12 cells induces morphological differentiation. Cell 42, 841–848.

Brown, M. S. and Goldstein, J. L. (1980). Multivalent feedback regulation of HMG CoA reductase, a control mechanism coordinating isoprenoid synthesis and cell growth. J. Lipid Res. 21, 505–517.

Casey, P. J. (1992). Biochemistry of protein prenylation. J. Lipid Res. 33, 1731–1740.

Casey, P. J., Solski, P. A., Der, C. J., and Buss, J. E. (1989). p21ras is modified by a farnesyl isoprenoid. Proc. Natl. Acad. Sci. USA 86, 8323–8327.

Crick, D. C., Waechter, C. J., and Andres, D. A. (1994). Utilization of geranylgeraniol for protein isoprenylation in C6 glial cells. Biochem. Biophys. Res. Comm. 205, 955–961

Der, C. J., and Cox, A. D. (1991). Isoprenoid modification and plasma membrane association: critical factors for Ras oncogenicity. Cancer Cells 3, 331–340.

Epstein, W. W., Lever, D. C., Rilling, H. C. (1990). Synthesis of geranylgeranylcysteine and identification of this amino acid as a component of proteins in CHO cells. Proc. Natl. Acad Sci. USA 87, 7352–7354.

Farnsworth, C. C., Gelb, M. H., and Glomset, J. A. (1990). Identification of geranylgeranyl-modified proteins in HeLa cells. Science 247, 320–322.

Fenton, R. G., Kung, H-f., Longo, D. L., and Smith, M. R. (1992). Regulation of intracellular actin polymerization by prenylated proteins. J. Cell Biol. 117, 347–356.

Fukada, Y., Takao, T., Ohguro, H., Yoshizawa, T., Akino, T., and Shimonishi, Y. (1990). Farnesylated gamma-subunit of photoreceptor G protein indispensible for GTP-binding. Nature 346, 658–660.

Grünler, J., Ericsson, J., and Dallner, G. (1994). Branch-point reactions in the biosnthesis of cholesterol, dolichol, ubiquinone, and prenylated proteins. Biochim. Biophys. Acta 1212, 259–277.

Hancock, J. F., Magee, A. I., Childs, J. E., and Marshall, C. J. (1989) All ras proteins are polyisoprenylated but only some are palmitoylated. Cell 57, 1167–1177.

Holtz, D., Tanaka, R. A., Hartwig, J., and McKeon, F. (1989). The CaaX motif of lamin A functions in conjunction with the nuclear localization signal to target assembly to the nuclear envelope. Cell 59, 969–977.

Hori, Y., Kikuchi, A., Isomura, M., Katayama, M. Miura, Y., Fujioka, H., Kaibuchi K., and Takai, Y. (1991). Post-translational modifications of the C-terminal region of the Rho protein are important for its interaction with membranes and the stimulatory and inhibitory GDP/GTP exchange proteins. Oncogene 6, 515–522.

Illingworth, D. R., and Bacon, S. (1989). Treatment of heterozygous familial hypercholesterolemia with lipid-lowering drugs. Arteriosclerosis 9, I-121–1134.

Inglese, J., Glickman, J. F., Lorenz, W. Caron, M., and Lefkowitz, R. J (1992). Isoprenylation of a protein kinase: requirement of farnesylation/alpha-carboxyl methylation for full enzymatic activity of rhodopsin kinase. J. Biol. Chem. 267, 1422–1425.

James, G. L., Goldstein, J. L., and Brown, M. S. (1995) Polylysine and CVIM sequences of K-RasB dictate specificity of prenylation and confer resistance to benzodiazepine peptidomimetic in vitro. J. Biol. Chem. 270, 6221–6226.

Kato, K., Cox, A. D., Hisaka, M. M., Graham, S. M., Buss, J. E., Der, C. J (1992). Isoprenoid addition to Ras protein is the critical modification for its membrane association and transforming activity. Proc. Natl. Acad Sci. USA 89, 6403–6407.

Leonard, S., Beck, L., Sinensky, M. (1990). Inhibition of isoprenoid biosynthesis and the posttranslational modification of pro-p21 ras. J. Biol. Chem. 265, 5157–5160.

Lerner, E. C., Qian, Y., Blaskovich, M. A., Fossum, R. D., Vogt, A., Sun, J., Cox, A. D. Der, C. J., Hamilton, A. D. and Sebti S. M. (1995a). Ras CAAX peptidomirnetic FTI-277 selectively blocks oncogenic Ras signaling by inducing cytoplasmic accumulation of inactive Ras-Raf complexes. J. Biol. Chem. 270, 26802–26806.

Lerner, E., Qian, Y., Hamilton, A. D., and Sebti, S. M. (199Sb). Disruption of oncogenic K-Ras4B processing and signaling by a potent geranylgeranyltransferase I inhibitor. J. Biol. Chem. 270, 26770–26773.

Maltese, W. A. (1990). Posttranslational modification of proteins by isoprenoids in mammalian cells. FASEB J. 4, 3319–3328.

McCormick, F. (1993). How receptors turn Ras on. Nature 363, 15–16.

McGuire, T. F., Corey, S., and Sebti, S. M. (1993). Lovastatin inhibits platelet-derived growth factor (PDGF)

stimulation of phosphatidylinositol 3-kinase activity as well as association of p85 subunit to tyrosine-phosphorylated PDGF receptor. J. Biol. Chem. 268, 22227–22230.

Mulcahy, L. S., Smith, M. R., and Stacey, D. W. (1985). Requirement for ras proto-oncogene function during serum-stimulated growth of NIH-3T3 cells. Nature 313, 241–243.

Nobes, C. D., and Hall, A. (1995). Rho, rac, and cdc42 GTPases regulate the assembly of multimolecular focal complexes associated with actin stress fibers, lamellipodia, and filopodia. Cell 81, 53–62.

Olson, M. F., Ashworth, A., and Hall, A. (1995). An essential role for rho, rac, and cdc42 GTPases in cell cycle progression through $G_1$. Science 269, 1270–1272.

Quesney-Huneeus V., Wiley, M. H., and Siperstein, M. D. (1979). Essential role for mevalonate synthesis in DNA replication. Proc. Natl Acad. Sci. USA 76, 5056–5060.

Reddy E P. Reynolds, R. K., Santos, E. and Barbacid, M. (1982). A point mutation is responsible for the acquisition of transforming properties by the T24 human bladder carcinoma oncogene. Nature 300, 149–152.

Reiss Y Brown, M. S., and Goldstein, J. L. (1992). Divalent cation and prenyl pyrophosphate specificities of the protein farnesyltransferase from rat brain, a zinc metalloenzyme. J. Biol. Chem 267, 6403–6408.

Sabine, J. R. (1983). 3-Hydroxy-3-methylglutaryl coenzyme A reductase. CRC Press, Boca Raton Fla.

Seabra M. C., Reiss, Y., Casey, P. J., Brown, M. S and Goldstein, J. L. (1991). Protein farnesyltransferase and geranylgeranyltransferase share a common a subunit. Cell 65, 429–434

Sebti, S M., Tkalcevic, G. T., and Jani, J. P. (1991). Lovastatin, a cholesterol biosynthesis inhibitor inhibits the growth of human H-ras oncogene transformed cells in nude mice. Cancer Comm 3, 141–147.

Sinensky M., and Logel, J. (1985). Defective macromolecule biosynthesis and cell-cycle progression in a mammalian cell starved for mevalonate. Proc. Natl. Acad. Sci. USA 82, 3257–3261.

Sun J., Qian Y., Hamilton, A. D., and Sebti S. M. (1995) Ras CAAX peptidomimetic FTI276 selectively blocks tumor growth in nude mice of a human lung carcinoma with K-Ras mutation and p53 deletion. Cancer Res. 55, 4243–4247.

What is claimed is:

1. A method of treating cancer related to aberrant H-Ras signaling sensitive to the combination below, in a mammal in need of treatment, comprising the co-administration of lovastatin and geranylgeraniol in effective amounts such that aberrant or oncogenic Ras signaling is inhibited without excessive cell toxicity.

2. The method of claim 1 wherein said mammal is a human.

3. The method of claim 1 wherein the cancer is selected from the group consisting of colorectal, pancreatic and lung cancer, and melanoma.

4. A method of treating restenosis in an individual in need of treatment comprising the co-administration of lovastatin and geranylgeraniol in effective amounts such that aberrant or oncogenic Ras signaling is inhibited without excessive cell toxicity.

5. A method of treating hepatitis delta virus infection in an individual in need of treatment comprising the co-administration of lovastatin and geranylgeraniol in effective amounts such that aberrant or oncogenic Ras signaling is inhibited without excessive cell toxicity.

6. A method of inhibiting Ras signaling in mammalian cells without excessive cell toxicity comprising administering an effective amount of lovastatin together with an effective amount of geranylgeraniol.

7. The method of claim 6 wherein said mammalian cells are human cells.

8. A pharmaceutical composition comprising lovastatin and geranylgeraniol in an effective proportion such that administration of said composition to an individual will inhibit aberrant or oncogenic Ras signaling without excessive cell toxicity.

* * * * *